United States Patent
Komori et al.

(10) Patent No.: US 12,037,467 B2
(45) Date of Patent: Jul. 16, 2024

(54) OIL-IN-WATER-TYPE EMULSION COMPOSITION, METHOD FOR PRODUCING SAME, AND USE OF SAME

(71) Applicant: DOW TORAY CO., LTD., Tokyo (JP)

(72) Inventors: Hideaki Komori, Ichihara (JP); Kazuhiko Kojima, Ichihara (JP); Takatoshi Toyama, Ichihara (JP); Hidetoshi Kondo, Ichihara (JP)

(73) Assignee: Dow Toray Co., Ltd., Tokyo (JP)

( * ) Notice: Subject to any disclaimer, the term of this patent is extended or adjusted under 35 U.S.C. 154(b) by 940 days.

(21) Appl. No.: 16/633,446

(22) PCT Filed: Jul. 9, 2018

(86) PCT No.: PCT/JP2018/025908
§ 371 (c)(1),
(2) Date: Apr. 5, 2020

(87) PCT Pub. No.: WO2019/021800
PCT Pub. Date: Jan. 31, 2019

(65) Prior Publication Data
US 2020/0308350 A1   Oct. 1, 2020

(30) Foreign Application Priority Data
Jul. 24, 2017   (JP) .................. 2017-142400

(51) Int. Cl.
| | |
|---|---|
| C08J 3/05 | (2006.01) |
| A61K 8/06 | (2006.01) |
| A61K 8/891 | (2006.01) |
| C08J 3/03 | (2006.01) |
| C09D 5/02 | (2006.01) |
| C09D 183/04 | (2006.01) |
| D06M 15/643 | (2006.01) |
| B01F 27/92 | (2022.01) |
| C08J 3/07 | (2006.01) |

(52) U.S. Cl.
CPC ............... *C08J 3/03* (2013.01); *A61K 8/062* (2013.01); *A61K 8/891* (2013.01); *C09D 5/022* (2013.01); *C09D 183/04* (2013.01); *D06M 15/643* (2013.01); A61K 2800/21 (2013.01); B01F 27/92 (2022.01); C08J 3/05 (2013.01); C08J 3/07 (2013.01); C08J 2383/04 (2013.01)

(58) Field of Classification Search
CPC ............ C08J 3/05; C08J 3/03; C08J 2383/04
See application file for complete search history.

(56) References Cited

U.S. PATENT DOCUMENTS

| | | | | |
|---|---|---|---|---|
| 4,788,001 A | * | 11/1988 | Narula | A61Q 19/00 516/74 |
| 5,726,270 A | * | 3/1998 | Craig | C08G 77/06 524/837 |
| 5,806,975 A | | 9/1998 | Hosokawa et al. | |
| 2006/0135626 A1 | | 6/2006 | Shim et al. | |
| 2012/0053290 A1 | | 3/2012 | Barnes et al. | |
| 2017/0204266 A1 | * | 7/2017 | Kennedy | A61K 8/894 |

FOREIGN PATENT DOCUMENTS

| | | |
|---|---|---|
| AU | 730772 B2 | 3/2001 |
| EP | 1013700 A2 | 6/2000 |
| JP | H09124797 A | 5/1997 |
| JP | 2001239141 A | 9/2001 |
| JP | 2006263728 A | 10/2006 |
| JP | 2006528714 A | 12/2006 |
| JP | 2012526893 A | 11/2012 |
| JP | 2013095834 A | 5/2013 |
| JP | 2013095835 A | 5/2013 |
| WO | 2013065766 A1 | 5/2013 |
| WO | 2013065767 A1 | 5/2013 |

OTHER PUBLICATIONS

NANOVisK product sheet, 2022.*
English translation of International Search Report for PCT/JP2018/025908 dated Oct. 9, 2018, 2 pages.
Machine assisted English translation of JP2001239141A obtained from https://patents.google.com/patent on Apr. 20, 2020, 10 pages.
Machine assisted English translation of JP2006263728A obtained from https://patents.google.com/patent on Apr. 20, 2020, 6 pages.

* cited by examiner

*Primary Examiner* — Margaret G Moore
(74) *Attorney, Agent, or Firm* — Warner Norcross + Judd LLP

(57) ABSTRACT

Provided is an oil-in-water-type emulsion composition which can be produced by directly emulsifying an organopolysiloxane having a high polymerization degree, contains substantially no oversized particle, and has a small average particle size. A method for producing the oil-in-water-type emulsion composition using a vertical batch mixer is also provided. The oil-in-water-type emulsion composition is an emulsion comprising (A) an organopolysiloxane having an overall viscosity of 1,000,000 mPa·s or more or having plasticity or a mixture thereof, (B) a surfactant, and (C) water. Component (A) is emulsified in water by the action of component (B), the average particle size of emulsion particles falls within the range from 0.1 to 7.5 μm, and the content of emulsion particles each having a particle size 10 times or more larger than the average particle size is less than 5.0 vol %.

15 Claims, 1 Drawing Sheet

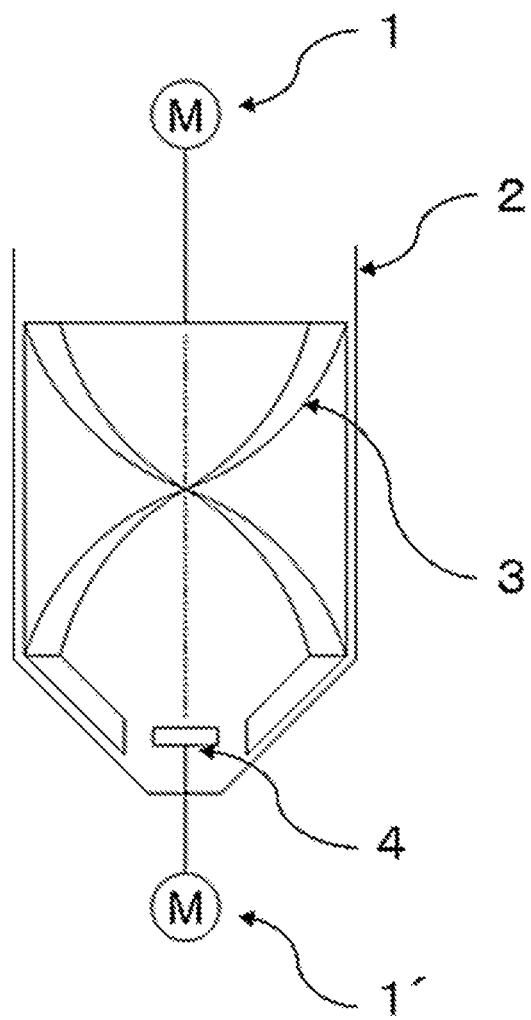

OIL-IN-WATER-TYPE EMULSION COMPOSITION, METHOD FOR PRODUCING SAME, AND USE OF SAME

CROSS-REFERENCE TO RELATED APPLICATIONS

This application is the National Stage of International Appl. No. PCT/JP2018/025908 filed on 9 Jul. 2018, which claims priority to and all advantages of Japanese Appl. No. 2017-142400 filed on 24 Jul. 2017, the content of which is hereby incorporated by reference.

TECHNICAL FIELD

The present invention relates to an oil-in-water type emulsion composition substantially free of oversized particles and having a small average particle size in which an organopolysiloxane with a high degree of polymerization has been directly polymerized, something difficult to realize using a method of the prior art. The present invention also relates to a method for producing this oil-in-water type emulsion composition using a vertical batch mixer, and to applications containing this composition, such as cosmetic ingredients, cosmetics, film-forming agents, coating agents, and fiber-treating agents.

BACKGROUND ART

Organopolysiloxane emulsions are widely used in industry as, for example, lubricants, mold release agents, fiber-treating agents, glass fiber-treating agents, cosmetic bases, polishes, and paint additives. Emulsions substantially free of oversized particles having a small average particle size and a narrow particle size distribution generally experience much less emulsion phase separation due to particle agglomeration and tend to have excellent handling, workability, and storage stability. Also, because emulsions obtained by the direct emulsification method can make full use of the expected properties of an organopolysiloxane, which is emulsified directly without, for example, a polymerization reaction, the organopolysiloxane can be selected knowing that emulsion particles substantially free of low molecular weight siloxane oligomers can be designed.

Organopolysiloxanes with a high degree of polymerization (high-viscosity silicone oils, silicone gums with a degree of plasticity that is difficult to measure using a rotational viscometer, and mixtures thereof) have excellent film-forming properties, adhesion to hair and fibers and treatment efficiency, and improve the flatness and smoothness of film when used as a coating agent or coating additive. These organopolysiloxanes can be difficult to emulsify directly, though various emulsification methods have been proposed (see, for example, Patent Documents 1-2).

However, the methods proposed in Patent Document 1 and Patent Document 2 can only be used to realize an oil-in-water emulsion composition of silicone gum having an average particle size of 9 μm or less. For example, an oil-in-water emulsion composition having an average particle size of 9.9 μm was disclosed in an example of Patent Document 1, and an oil-in-water emulsion composition having an average particle size of 23.4 μm or 27.9 μm was disclosed in Example 1 of Patent Document 2. The stability of the emulsion particles was poor because they contained a large amount of oversized particles with a particle size much larger than the average particle size. An emulsion with a small particle size was realized in Patent Document 2 (Example 2) by dispersing and emulsifying a silicone resin with a high degree of polymerization in a xylene solvent, but the apparent viscosity of the oil phase constituting the emulsion particles declined significantly in this method and the solvent used in the dilution process could not be removed in some cases. The anticipated technical effects sometimes cannot be realized when organopolysiloxane emulsions with a high degree of polymerization are added, and these emulsions sometimes cannot be used, for example, as a cosmetic ingredient.

An emulsion polymerization-type oil-in-water emulsion composition comprising an organopolysiloxane with a high degree of polymerization and containing emulsion particles with an average particle size below 1.0 μm was proposed in Patent Document 3, which was obtained by subjecting a reactive organopolysiloxane to emulsion polymerization. However, oil-in-water emulsion compositions obtained using an emulsion polymerization reaction require the use of a polymerization-reactive surfactant, and a large amount of volatile, low molecular weight siloxane oligomers remain in the system as byproducts of the emulsion polymerization reaction. As a result, there are limitations on the applications in which they can be used and on compositions that can be designed.

In order to obtain an organopolysiloxane with a high degree of polymerization substantially free of oversized particles and having a small particle size using the direct emulsification method, a not-yet realized oil-in-water emulsion that does not produce volatile siloxane oligomer byproducts and a method for advantageously producing this emulsion would be required.

Vertical batch mixers used to directly emulsify oils have been disclosed in Patent Documents 4-5, but neither one mentions or suggests the advantages in relation to direct emulsification methods for organopolysiloxanes with a high degree of polymerization.

PRIOR ART DOCUMENTS

Patent Documents

Patent Document 1: JP H09-124797 A
Patent Document 2: JP 2006-528714 A
Patent Document 3: JP 2012-526893 A
Patent Document 4: JP 2001-239141 A
Patent Document 5: JP 2006-263728 A

BRIEF DESCRIPTION OF THE DRAWINGS

FIG. 1 is a vertical cross-sectional view of a vertical batch mixer that can be used in the present invention.

SUMMARY OF THE INVENTION

Problem to be Solved by the Invention

It is an object of the present invention to solve this problem by providing an oil-in-water type emulsion composition substantially free of oversized particles and having a small average particle size in which an organopolysiloxane with a high degree of polymerization has been directly polymerized. It is another object of the present invention to provide applications and an industrially advantageous production method for this oil-in-water type emulsion composition.

Means for Solving the Problem

The present invention is a result of extensive research conducted by the present inventors to solve this problem.

One object of the present invention has been achieved by a directly emulsified oil-in-water emulsion composition comprising: an organopolysiloxane with a high degree of polymerization, in which the average particle size is in a range from 0.1 to 7.5 µm, the amount of emulsion particles having a particle size of at least 10 times the average particle size in the particle size distribution of the emulsion is less than 5.0% by volume, and the apparent viscosity at 25° C. of the oil phase constituting the emulsion particles is at least 1,000,000 mPa·s or has plasticity. The problem is also solved by applications containing this oil-in-water emulsion composition, such as cosmetic ingredients, cosmetics, film-forming agents, coating agents, and fiber-processing agents, and by an advantageous method for producing this oil-in-water emulsion composition by mechanically emulsifying an organopolysiloxane in water using a vertical batch mixer.

Specifically, the present invention is the following.

[1] An oil-in-water emulsion composition comprising:
(A) 100 parts by mass of an organopolysiloxane having an overall viscosity at 25° C. of at least 1,000,000 mPa·s or having plasticity or a mixture thereof,
(B) 0.1 to 30 parts by mass of at least one type of surfactant, and
(C) 100 to 2,000 parts by mass of water;
wherein
component (A) is emulsified in water by component (B) to obtain an emulsion,
the average particle size of the emulsion particles measured using the laser diffraction/scattering method is in a range from 0.1 to 7.5 µm,
the amount of emulsion particles having a particle size of at least 10 times the average particle size in the particle size distribution of the emulsion is less than 5.0% by volume, and
the apparent viscosity at 25° C. of the oil phase (component (A)) constituting the emulsion particles is at least 1,000,000 mPa·s or has plasticity.

[2] An oil-in-water emulsion composition according to [1], wherein component (A) is selected from a
(A1) an organopolysiloxane having an overall viscosity at 25° C. of at least 1,000,000 mPa·s or having plasticity, or
(A2) an organopolysiloxane mixture having an overall viscosity at 25° C. of at least 1,000,000 mPa·s or having plasticity.

[3] An oil-in-water emulsion composition according to [1] or [2], wherein component (A) is an organopolysiloxane having an overall viscosity at 25° C. of at least 2,500,000 mPa·s or having plasticity or a mixture thereof.

[4] An oil-in-water emulsion composition according to any one of [1] to [3], wherein the sum of the amount of the siloxane oligomers having a siloxane degree of polymerization of 3 to 6 in the oil phase constituting the emulsion composition is less than 1.0% by mass.

[5] An oil-in-water emulsion composition according to any one of [1] to [4], wherein component (B) comprises (B1) a nonionic surfactant and (B2) an ionic surfactant, the mass ratio of component (B1) to component (B2) is 100:0 to 50:50, and the amount of component (B) used is in a range from 0.5 to 15 parts by mass per 100 parts by mass of component (A).

[6] A cosmetic ingredient comprising an oil-in-water emulsion composition according to any one of [1] to [5].

[7] A cosmetic comprising an oil-in-water emulsion composition according to any one of [1] to [5].

[8] A film-forming agent comprising an oil-in-water emulsion composition according to any one of [1] to [5].

[9] A coating or coating composition comprising an oil-in-water emulsion composition according to any one of [1] to [5].

[10] A fiber-treating agent comprising an oil-in-water emulsion composition according to any one of [1] to [5].

[11] A method for producing an oil-in-water emulsion composition according to any one of [1] to [5], the method comprising mechanically emulsifying (A) an organopolysiloxane having an overall viscosity at 25° C. of at least 1,000,000 mPa·s or having plasticity or a mixture thereof using (B) at least one type of surfactant in (C) water using a vertical batch mixer.

[12] A method for producing an oil-in-water emulsion composition according to [11], wherein the vertical batch mixer is a concentric multiple shaft vertical batch mixer having multiple rotating shafts arranged along the same shaft core, and comprising a ribbon-shaped stirring blade arranged on at least one rotating shaft and a non-ribbon-shaped stirring blade arranged on a rotating shaft different from this rotating shaft.

[13] A method for producing an oil-in-water emulsion composition according to [11] or [12], wherein the method is a direct emulsification method using a vertical batch mixer that does not involve an emulsion polymerization reaction.

Effects of the Invention

The present invention is able to provide an oil-in-water type emulsion composition substantially free of oversized particles and having a small average particle size in which an organopolysiloxane with a high degree of polymerization has been directly polymerized. The present invention is also able to provide applications for this oil-in-water type emulsion composition, such as cosmetic ingredients, cosmetics, film-forming agents, coating agents, and fiber-treating agents. The present invention is also able to provide an industrially advantageous production method for this oil-in-water type emulsion composition.

Embodiment of the Invention

Oil-in-Water Emulsion Composition

The following is a description of an oil-in-water emulsion composition of the present invention.

(A) Organopolysiloxane or Mixture Thereof

Component (A) is an oil phase component constituting the emulsion particles of the present emulsion, and is an organopolysiloxane or a mixture thereof having an overall viscosity at 25° C. of at least 1,000,000 mPa·s or plasticity. Component (A) has an overall viscosity at 25° C. of at least 1,000,000 mPa·s or plasticity as measured in accordance with the method specified in JIS K6249. (In the present invention, "plasticity" refers to the value under a 1 kgf load applied to a 4.2 g spherical sample at 25° C. for three minutes.) It is preferably a raw rubbery organopolysiloxane whose plasticity is in a range from 50 to 200, more preferably in a range from 80 to 180. The raw rubber-like organopolysiloxane whose plasticity as described above can be measured is sometimes referred to as "silicone gum". The viscosity of organopolysiloxanes having plasticity are usually difficult to measure using a device such as a rotational viscometer, and tend to have a high viscosity of 5,000,000 mPa·s or higher if the viscosity can be measured at 25° C.

The organopolysiloxane or mixture thereof in component (A) may be an organopolysiloxane mixture containing a silicone resin (including silicone resin fine particles) or a silicone elastomer (including silicone elastomer fine particles). There are no particular restrictions other than the overall viscosity. The organopolysiloxane used in the present invention can contain additives such as silica fine particles and a thickener, if necessary, in an amount that does not impair the object of the present invention, and may even be a high-viscosity silicone compound containing an organopolysiloxane (including antifoaming compounds). Long-lasting antifoaming properties depend on the viscosity of the defoaming agent, and usually last longer when the viscosity or viscousness is higher. This is probably due to the fact that the size of the defoaming agent particles is difficult to change in a foaming system. The defoaming agent has to be widely dispersed in the foaming system in order to realize antifoaming properties, but it is difficult to make the particle size of a highly viscous defoaming agent finer and closer to the optimum particle size so as to more readily disperse the defoaming agent. However, an oil-in-water emulsion composition of the present invention can form a stable and finer emulsion using a high-viscosity defoaming compound, and can be expected to have improved, longer-lasting defoaming performance. However, component (A) cannot contain additives such as silica particles, silicone resin particles and silicone elastomer particles that exceed the upper limit for the average particle size of the emulsion particles of the present invention.

There are no particular restrictions on the organopolysiloxane or mixture thereof in component (A), which may have a divalent organic group between siloxane units (such as a silalkylene group, silphenylene group, or polyoxyalkylene group), and may include a tris (trialkylsiloxy) siloxy group-containing organic group, a carbosiloxane dendrimer structure-containing organic group, or a polysiloxane structure-containing organic group linked by a divalent organic group. An organopolysiloxane or mixture thereof in component (A) may preferably have a functional group selected from among organic modifying group obtained when hydroxyl groups, alkoxy groups, monovalent hydrocarbon groups, and optionally some hydrogen atoms bonded to monovalent hydrocarbon groups are substituted with amino groups, epoxy groups, carboxyl groups, and halogen atoms, etc.

An organopolysiloxane or mixture thereof in component (A) can preferably be a compound represented by the following general formula.

$$R_a SiO_{(4-a)/2}$$

In this formula, R is a group selected from among a hydroxyl group, an alkoxy group having 1 to 3 carbon atoms, and a substituted or unsubstituted monovalent hydrocarbon group. Examples include a hydroxyl group; an alkoxy group such as a methoxy group, an ethoxy group, and a propoxy group; an alkyl group having 1 to 30 carbon atoms such as a methyl group, an ethyl group, or a propyl group; an aryl group having 6 to 30 carbon atoms such as a phenyl group or a tolyl group; an aralkyl group such as a benzyl group; and a halogenated alkyl group such as chloromethyl group or 3,3,3-trifluoropropyl group in which some or all of the carbon-bonded hydrogen atoms of these groups are substituted with halogen atoms. Also, a is an integer from 1.9 to 2.1. When a is within this group, it means the organopolysiloxane in component (A) may have branches but primarily has a linear structure consisting substantially of diorganosiloxy units (D units). The molecular structure may be linear, partially branched linear, or reticulated. Among these, a linear organopolysiloxane is preferably used. The degree of siloxane polymerization is preferably from about 3,000 to 20,000.

Examples of organopolysiloxanes include dimethylpolysiloxane capped at both ends with trimethylsiloxy groups, dimethylpolysiloxane capped at both ends with silanol groups, dimethylsiloxane/phenylmethylsiloxane copolymers capped at both ends with a trimethylsiloxane group, dimethylsiloxane/phenylmethylsiloxane copolymers capped at both ends with a silanol group, dimethylsiloxane/diphenylsiloxane copolymers capped at both ends with a trimethylsiloxy group, dimethylsiloxane-diphenylsiloxane copolymers capped at both ends with a silanol group, dimethylsiloxane/methyl (3,3,3-trifluoropropyl) siloxane copolymers capped at both ends with a trimethylsiloxy group, and dimethylsiloxane/methyl (3,3,3-trifluoropropyl) siloxane copolymers capped at both ends with a silanol group. These organopolysiloxanes may have a structure in which some of the methyl groups have been substituted with an alkyl group having 6 to 20 carbon atoms, an aminoalkyl group having 3 to 15 carbon atoms, a perfluoroalkyl group having 3 to 15 carbon atoms, a quaternary ammonium base-containing alkyl group having 3 to 15 carbon atoms, an epoxy group, a carboxyl group, a polysiloxane structure-containing organic group linked by a silicon atom and a divalent organic group, a tris (trialkylsiloxy) siloxy group-containing organic group linked by a silicon atom and a divalent organic group, and a carbosiloxane dendrimer structure-containing organic group linked by a silicon atom and a divalent organic group. From the standpoint of adhesion to hair, an oil-in-water emulsion used in hair care applications may include an organopolysiloxane having an amino group such as a 3-aminopropyl group or an N-(2-aminoethyl) 3-aminopropyl group.

An oil-in-water emulsion of the present invention is preferably subjected to a direct emulsification method not involving an emulsion polymerization reaction. In this way, low molecular weight siloxane oligomers are not a byproduct produced in component (A) or in the oil phase of the emulsion particles obtained by emulsifying this component, and an oil-in-water emulsion can be designed that is substantially free of siloxane oligomers. More specifically, by removing low molecular weight siloxane oligomers from component (A) by means such as stripping before emulsification, an oil-in-water emulsion composition can be obtained in which the sum of the amount of siloxane oligomers having a degree of siloxane polymerization of 3 to 6 in the oil phase constituting the emulsion composition is less than 1.0% by mass. The sum of the amount of these siloxane oligomers can also be less than 0.75 mass %, less than 0.50 mass %, or less than 0.10 mass %. If an oil-in-water emulsion of an organopolysiloxane having a high degree of polymerization equivalent to that of component (A) is obtained using an emulsion polymerization reaction, siloxane oligomers are present as a byproduct in the oil phase in an amount exceeding 1.0% by mass because an emulsion polymerization reaction is an equilibrium reaction. Because the emulsion particles are dispersed in water, they can be difficult to remove structurally. In the present invention, as mentioned above, an oil-in-water emulsion of an organopolysiloxane with a high degree of polymerization can be obtained which essentially solves these problems and has siloxane oligomers present in the oil phase in amounts below the detectable limit of 100 ppm or less.

Component (A) constituting the oil phase of the emulsion particles may be a single organopolysiloxane or may be a mixture of organopolysiloxanes. However, the organopolysiloxane or mixture thereof must have an oil phase with an apparent viscosity at 25° C. of at least 1,000,000 mPa·s or plasticity. This means that the overall viscosity of component (A) does not change before and after direct emulsification, and that component (A) directly constitutes the oil phase of the emulsion particles. By breaking up an oil-in-water emulsion of the present invention and extracting the oil phase using a known method, the apparent viscosity at 25° C. of the oil phase of the emulsion particles or the plasticity, which are not easily measured, can be confirmed.

Preferably, component (A) is selected from (A1) an organopolysiloxane having an overall viscosity at 25° C. of at least 1,000,000 mPa·s or having plasticity, or (A2) an organopolysiloxane mixture having an overall viscosity at 25° C. of at least 1,000,000 mPa·s or having plasticity. Component (A) preferably has an overall viscosity at 25° C. of at least 2,500,000 mPa·s or has plasticity, but may have a viscosity at 25° C. of at least 5,000,000 mPa·s or have plasticity. Especially preferred is a raw rubber-like organopolysiloxane (=silicone gum) having an overall viscosity at 25° C. of at least 5,000,000 mPa·s or having plasticity.

Component (A) in an oil-in-water emulsion composition of the present invention can be obtained by adding (A') an organopolysiloxane or a mixture thereof having an apparent viscosity at 25° C. of less than 1,000,000 mPa·s and a polymerization reaction catalyst to an emulsifier, preferably a vertical batch mixer described below, and conducting a polymerization reaction by stirring at room temperature or under heat to synthesize component (A) with the proper degree of polymerization. Specifically, the polymerization reaction for component (A) in an oil-in-water emulsion composition of the present invention is preferably conducted in an emulsifier, preferably a vertical batch mixer described below to obtain a mixture of organopolysiloxanes having an overall viscosity of at least 1,000,000 mPa·s or plasticity, which is then emulsified. As in the case of component (A), component (A') may be an organopolysiloxane mixture containing a silicone resin or silicone elastomer as long as the apparent viscosity conditions are satisfied. Component (A') as a raw material of component (A), may contain additives such as silica fine particles and a thickener, if necessary, as long as the object of the present invention is not impaired.

Component (A') as a precursor for synthesizing component (A) may be a single organopolysiloxane or a mixture of two or more organopolysiloxanes. There are no particular restrictions on the type of polymerization reaction used to obtain component (A), and examples include a condensation reaction, a hydrosilylation reaction, or a radical polymerization reaction. The emulsifier in the present invention is preferably a vertical batch mixer, and by conducting the polymerization reaction inside the emulsifier, the synthesis reaction and emulsification of component (A) can be conveniently conducted in a single device.

When the polymerization reaction is a condensation reaction, the (A') organopolysiloxane or mixture thereof with a viscosity at 25° C. of less than 1,000,000 mPa·s preferably has a polymerizable reactive group in the molecule such as a hydroxyl group (silanol group). Examples having an apparent viscosity at 25° C. of less than 1,000,000 mPa·s, and preferably an apparent viscosity at 25° C. in a range from 5,000 to 100,000 mPa·s, include dimethylpolysiloxane capped at both ends with a silanol group, dimethylsiloxane/phenylmethylsiloxane copolymers capped at both ends with a silanol group, dimethylsiloxane-diphenylsiloxane copolymers capped at both ends with a silanol group, dimethylsiloxane/methyl (3,3,3-trifluoropropyl) siloxane copolymers capped at both ends with a silanol group, and mixtures thereof. The other functional groups and structural features are those of component (A) described above. Component (A) obtained by polymerizing component (A') has an emulsion polymerizable reactive group such as a hydroxyl group (silanol group) in the molecule, in particular at the end of the molecular chain, and the viscosity at 25° C. may be in a range from 1,000,000 mPa·s to 5,000,000 mPa·s.

The method used to polymerize component (A') can be any method used to perform a polymerization reaction on an organopolysiloxane having a silanol group on both ends, such as a polymerization method using an ionic surfactant as a polymerization catalyst. For example, an organopolysiloxane capped at both ends with a silanol group having a viscosity at 25° C. of less than 1,000,000 mPa·s or a mixture thereof and a polymerization reaction catalyst that is an ionic surfactant such as an aqueous solution of alkylbenzene sulfonic acid can be added to an emulsifier, preferably a vertical batch mixer, and mixed together while stirring at a temperature in a range from room temperature to 90 degrees to obtain component (A) as an organopolysiloxane or a mixture thereof having a higher viscosity than the organopolysiloxane or mixture that is the precursor of component (A).

(B) Surfactant

Component (B) is one or more surfactants used to emulsify component (A) in water. In the emulsion particles of the present invention, at least some of component (B) is present at the interface between component (A) serving as the oil phase and component (C) serving as the aqueous phase so that component (B) forms emulsion particles and thus an oil-in-water emulsion in which component (A) is dispersed in the aqueous phase.

There are no particular restrictions on the type of surfactant used, which can be a nonionic (nonionic) surfactant; an ionic surfactant selected from among anionic surfactants, amphoteric surfactants, and cationic surfactants; and a semipolar surfactant. When an oil-in-water emulsion composition of the present invention is a direct emulsion in which component (A) is emulsified in water by component (B), unlike an emulsion polymerization-type emulsion, an ionic surfactant is not required. In other words, emulsification may be performed using component (B) consisting of (B1) a nonionic surfactant and (B2) an ionic surfactant, in which the mass ratio of component (B1) to component (B2) may be in a range from 100:0 to 50:50, or 100:0 when using component (B1) alone. These surfactants and semipolar surfactants may also be used in combination. Some of the surfactant may remain in the aqueous phase as a cleaning component, such as in a cosmetic ingredient. When an oil-in-water emulsion composition of the present invention contains a high molecular weight polysiloxane component (A) obtained by polymerizing component (A') in an emulsifier, an ionic surfactant may be used as the polymerization catalyst.

(B1) Nonionic Surfactants

Examples of nonionic surfactants include polyoxyalkylene ethers, polyoxyalkylene alkyl ethers, polyoxyalkylene fatty acid esters (for example, those composed of polyethylene glycol (or ethylene oxide) and higher fatty acids (such as linear or branched fatty acids having 12 to 18 carbon atoms)), polyoxyalkylene fatty acid diesters, polyoxyalkylene resin acid esters, polyoxyalkylene (hardened) castor oils, polyoxyalkylene alkylphenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters (for example, those composed of sorbitan, polyethylene glycol, and higher fatty acids (such as straight or branched fatty acids having 12 to 18 carbon atoms)), polyoxyalkylene sorbitan fatty acid esters, polyoxyalkylene sorbite fatty acid esters, polyoxyalkylene glycerin fatty acid esters, polyglycerin alkyl ethers, polyglycerin fatty acid esters, sucrose fatty acid esters, fatty acid alkanolamides, alkyl glucosides, polyoxyalkylene fatty acid bisphenyl ethers, polypropylene glycol, diethylene glycol, polyoxyalkylene-modified silicones, polyglyceryl-modified silicones, glyceryl-modified silicones, sugar-modified silicones, fluorinated surfactants, polyoxyethylene/polyoxypropylene block polymers, and alkyl polyoxyethylene/polyoxypropylene block polymer ethers. Especially preferred are polyoxyalkylene-modified silicones, polyglyceryl-modified silicones, and glyceryl-modified silicones having alkyl branches and straight-chain silicone branches simultaneously provided with hydrophilic groups when necessary. The HLB of these nonionic surfactants can be selected based on the emulsification conditions.

(B2-1) Anionic Surfactants

Examples of anionic surfactants include saturated or unsaturated fatty acid salts (such as sodium laurate, sodium stearate, sodium oleate, or sodium linolenate), alkyl sulfates, alkylbenzenesulfonic acids (such as hexylbenzenesulfonic acid, octylbenzenesulfonic acid, or dodecylbenzenesulfonic acid) and salts thereof, polyoxyalkylene alkyl ether sulfates, polyoxyalkylene alkenyl ether sulfates, polyoxyethylene alkyl sulfates, alkyl sulfosuccinates, polyoxyalkylene sulfosuccinic acid alkyl ester salts, polyoxyalkylene alkyl phenyl ether sulfates, alkane sulfonates, octyltrimethylammonium hydroxides, dodecyl trimethylammonium hydroxides, alkyl sulfonates, polyoxyethylene alkyl phenyl ether sulfates, polyoxyalkylene alkyl ether acetates, alkyl phosphates, polyoxyalkylene alkyl ether phosphates, acyl glutamates, α-acyl sulfonates, alkyl sulfonates, alkyl allyl sulfonates, α-olefin sulfonates, alkyl naphthalene sulfonates, alkane sulfonates, alkyl or alkenyl sulfates, alkyl amide sulfates, alkyl or alkenyl phosphates, alkylamidophosphates, alkyloylalkyltaurine salts, N-acyl amino acid salts, sulfosuccinates, alkyl ether carboxylates, amide ether carboxylates, α-sulfo fatty acid ester salts, alanine derivatives, glycine derivatives, and arginine derivatives. Examples of salts include alkali metal salts such as sodium salts, alkaline earth metal salts such as magnesium salts, alkanolamine salts such as triethanolamine salts, and ammonium salts.

(B2-2) Cationic Surfactants

Examples of cationic surfactants include alkyl trimethyl ammonium chloride, stearyl trimethyl ammonium chloride, lauryl trimethyl ammonium chloride, cetyl trimethyl ammonium chloride, alkyl trimethyl ammonium chloride tallow, behenyl trimethyl ammonium chloride, stearyl trimethyl ammonium bromide, behenyl trimethyl ammonium bromide, distearyl dimethyl ammonium chloride, dicocoyl dimethyl ammonium chloride, dioctyl dimethyl ammonium chloride, dicocoyl dimethyl ammonium chloride, dioctyl dimethyl ammonium chloride, di (POE) oleyl methyl ammonium chloride (2EO), benzalkonium chloride, alkyl benzalkonium chloride, alkyl dimethyl benzalkonium chloride, benzethonium chloride, stearyl dimethyl benzyl ammonium chloride, lanolin-derived quaternary ammonium salts, diethyl aminoethylamide stearate, dimethyl aminopropylamide stearate, am idopropyldimethyl hydroxypropylammonium behenate chloride, stearoylcholaminoformyl methylpyridinium chloride, cetylpyridinium chloride, tall oil chloride alkylbenzylhydroxyethyl imidazolinium, and benzyl ammonium salts.

(B2-3) Amphoteric Surfactants

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples include imidazoline-type amphoteric surfactants such as 2-undecyl-N,N,N-(hydroxyethylcarboxymethyl)-2-imidazoline sodium and 2-cocoyl-2-imitazolinium hydroxide-1-carboxyethyloxy disodium salts; alkyl betaine-type amphoteric surfactants such as betaine lauryl dimethylaminoacetate and myristyl betaine; amidobetaine-type amphoteric surfactants such as coconut oil fatty acid amidopropyldimethylaminoacetic acid betaine, palm kernel oil fatty acid amidopropyldimethylaminoacetic acid betaine, tallow fatty acid amidopropyldimethylaminoacetic acid betaine, hardened tallow fatty acid amidopropyldimethylaminoacetic acid betaine, betaine laurate amidopropyldimethylaminoacetate, betaine myristic acid amidopropyldimethylaminoacetate, betaine amidopropyldimethylaminoacetate palmitate, amidopropyl dimethyl dimethylaminoacetate betaine stearate, and amidopropyl oleic acid dimethylaminoacetic acid betaine; alkylsulfobetaine-type amphoteric surfactants such as coconut oil fatty acid dimethylsulfopropylbetaine; alkylhydroxysulfobetaine-type amphoteric surfactants such as lauryl dimethylaminohydroxysulfobetaine; phosphobetaine-type amphoteric surfactants such as lauryl hydroxyphosphobetaine; and amidoamino acid-type amphoteric surfactants such as N-lauroyl-N'-hydroxyethyl-N'-carboxymethylethylenediamine sodium, N-oleoyl-N'-hydroxyethyl-N'-carboxymethylethylenediamine sodium, N-cocoyl-N'-hydroxyethyl-N'-carboxymethylethylenediamine sodium, N-lauroyl-N'-hydroxyethyl-N'-carboxymethylethylenediamine potassium, N-oleoyl-N'-hydroxyethyl-N'-carboxymethylethylenediamine potassium, N-lauroyl-N-hydroxyethyl-N'-carboxymethylethylenediamine sodium, N-oleoyl-N-hydroxyethyl-N'-carboxymethylethylenediamine sodium, N-cocoyl-N-hydroxyethyl-N'-carboxymethylethylenediamine sodium, N-lauroyl-N-hydroxyethyl-N',N'-dicarboxymethylethylenediamine monosodium, N-oleoyl-N-hydroxyethyl-N',N'-dicarboxymethylethylenediamine monosodium, N-cocoyl-N-hydroxyethyl-N',N'-dicarboxymethylethylenediamine monosodium, N-lauroyl-N-hydroxyethyl-N',N'-dicarboxymethylethylenediamine disodium, N-oleoyl-N-hydroxyethyl-N',N'-dicarboxymethylethylenediamine disodium, and N-cocoyl-N-hydroxyethyl-N',N'-dicarboxymethylethylenediamine disodium.

(B3) Semi-Polar Surfactants

Examples of semi-polar surfactants include alkylamine oxide-type surfactants such as alkylamine oxide, alkylamidoamine oxide, and alkylhydroxyamine oxide. Use of alkyldimethylamine oxide with 10 to 18 carbon atoms or alkoxyethyldihydroxyethylamine oxide with 8 to 18 carbon atoms is especially preferred. Specific examples include dodecyl dimethylamine oxide, dimethyloctylamine oxide, diethyldecylamine oxide, bis-(2-hydroxyethyl) dodecylamine oxide, dipropyltetradecylamine oxide, methylethylhexadecylamine oxide, dodecylamidopropyldimethylamine oxide, cetyl dimethylamine oxide, stearyl dimethylamine oxide, tallow dimethylamine oxide, dimethyl-2-hydroxyoctadecylamine oxide, lauryl dimethylamine oxide, myristyl dimethylamine oxide, stearyl dimethylamine oxide, isostearyl dimethylamine oxide, coconut fatty acid alkyldimethylamine oxide, amidopropyl dimethylamine oxide caprylate, amidopropyl dimethylamine oxide caprate, lauric acid amidopropyl dimethylamine oxide, myristate amidopropyldimethylamine oxide, amidopropyldimethylamine palmitate, amidopropyl dimethylamine stearate, amidopropyl dimethylamine oxide isostearate, oleic acid amidopropyldimethylamine oxide, ricinoleic acid amidopropyl dimethylamine oxide, 12-hydroxystearic acid amidopropyldimethylamine oxide, coconut fatty acid amidopropyl dimethylamine oxide, palm kernel oil fatty acid amidopropyl dimethylamine oxide, castor oil fatty acid amidopropyl dimethylamine oxide, lauric acid amide ethyl dimethylamine oxide, myristate amidoethyl dimethylamine oxide, coconut fatty acid amidoethyl dimethylamine oxide, lauric acid amidoethyl diethylamine oxide, myristate amidoethyl diethylamine oxide, coconut fatty acid amidoethyl diethylamine oxide, lauric acid amide ethyl dihydroxyethylamine oxide, myristate amidoethyl dihydroxyethylamine oxide, and coconut fatty acid amidoethyl dihydroxyethylamine oxide.

There are no particular restrictions on the amount of surfactant used. All of component (B) per 100 parts by mass of the organopolysiloxane or mixture thereof serving as component (A) is usually in a range from 0.1 to 30 parts by mass, preferably in a range from 0.2 to 25 parts by mass or from 0.5 to 20 parts by mass, and may be in a range from 0.5 to 15 parts by mass. Component (B) may be divided and added in portions during emulsification. Here, the amounts mentioned above refer to the total amount of component (B) in the oil-in-water emulsion composition. Even when the amount of surfactant used in the present invention is relatively small, an oil-in-water emulsion composition can be obtained that contains almost no oversized particles. This is advantageous in that a good oil-in-water emulsion composition can be realized while also avoiding excessive use of surfactants. When the emulsification method of the present invention is not used, an emulsion containing a large amount of oversized particles is obtained using 15 parts by mass of surfactant and the practical emulsion stability is significantly impaired.

(C) Water

Component (C) is water, which is the dispersion medium used for the emulsion particles of component (A) emulsified by component (B) to form the aqueous phase of an oil-in-water emulsion composition of the present invention, and may optionally include other water-soluble components. The water is preferably clean and contains no components that inhibit emulsification and the storage stability of the oil-in-water emulsion composition. Examples include ion exchange water, distilled water, well water, and tap water.

The amount of water used per 100 parts by mass organopolysiloxane or mixture thereof in component (A) is in a range from 10 to 2,000 parts by mass, preferably in a range from 10 to 1000 parts by mass, more preferably in range from 10 to 500 parts by mass, and even more preferably in a range from 10 to 300 parts by mass. When an oil-in-water emulsion composition of the present invention is formed, water may be introduced as water for inverting the phase of component (A) and as dilution water after emulsion formation, or may be used in the successive addition of component (A) as an aqueous solution for surfactant (B) mentioned above. The water used to invert the phase of component (A) in an oil-in-water emulsion may be added all at once or may be added a little bit at a time in stages. After the oil-in-water emulsion has been formed with component (A) as the oil phase, dilution water may be added all at once or may be added a little bit at a time in stages. In some cases, the average particle size of emulsion particles obtained in the emulsification process can be reduced by adding the phase-inversion water and the dilution water in stages.

Optional Components

An oil-in-water emulsion composition of the present invention may include any additive desired as long as the object of the present invention is not impaired. Other additives that can be used include stabilizers, antioxidants (oxidation inhibitors), thickeners, pH adjusters, chelating agents, water-soluble alcohols, antiseptic preservatives, and antibacterial agents. The stability of an oil-in-water emulsion composition over time and the storage stability of the emulsion composition can be improved by adding small amounts of these additives. In the case of a cosmetic ingredient, the unpleasant odor from a surfactant can be masked by adding a fragrance.

Examples of antioxidants include tocopherol, butylhydroxyanisole, dibutylhydroxytoluene, and phytic acid; and examples of chelating agents include alanine, edetate sodium salt, sodium polyphosphate, sodium metaphosphate, and phosphoric acid.

Examples of thickeners include carboxyvinyl polymers, hydroxyethylcellulose, hydroxypropylmethylcellulose, methylcellulose, alginic acid, polyvinyl alcohols, polyvinylpyrrolidone, and sodium hyaluronate.

Examples of chelating agents include sodium edetate, citric acid, and salts thereof.

Examples of water-soluble alcohols include ethanol, isopropanol (IPA), butylene glycol, propylene glycol, and glycerin.

Examples of pH adjusters include lactic acid, citric acid, glycolic acid, succinic acid, tartaric acid, dl-malic acid, potassium carbonate, sodium bicarbonate, ammonium bicarbonate, hydrochloric acid, phosphoric acid, acetic acid, sulfuric acid, boric acid, borax, sodium hydroxide, potassium hydroxide, sodium carbonate, sodium hydrogen carbonate, and ammonia water.

Examples of antiseptic preservatives include alkyl paraoxybenzoate, benzoic acid, sodium benzoate, sorbic acid, potassium sorbate, and phenoxyethanol. Examples of antibacterial agents include benzoic acid, salicylic acid, carboxylic acid, sorbic acid, alkyl paraoxybenzoate, parachloromethcresol, hexachlorophen, benzalkonium chloride, chlorhexidine chloride, trichlorocarbanilide, triclosan, and photosensitizers. Examples of bacteriostatic agents include glyceryl monoalkyl ethers such as 1-heptyl glyceryl ether, 1-(2-ethylhexyl) glyceryl ether, 1-octyl glyceryl ether, 1-decyl glyceryl ether, and 1-dodecyl glyceryl ether.

Average Particle Size of Emulsion Particles

An oil-in-water emulsion composition of the present invention has an oil phase obtained by direct emulsification of the organopolysiloxane with high viscosity or plasticity in component (A), has emulsion particles with a small average particle size, and hardly has any oversized particles.

More specifically, in an oil-in-water emulsion composition of the present invention, the average particle size of the emulsion particles measured using the laser diffraction/scattering method (simply "the average particle size" below) is in a range from 0.1 to 7.5 µm, and the amount of emulsion particles having a particle size of at least 10 times the average particle size in the particle size distribution of the emulsion is less than 5.0% by volume. More preferably, the average particle size of the emulsion particles is in a range from 0.1 to 5.5 µm, and the amount of emulsion particles having a particle size of at least 10 times the average particle size is less than 5.0% by volume. The amount of emulsion particles having a particle size of at least 10 times the average particle size being less than 5.0% by volume means that, when viewing the particle size distribution of the oil-in-water emulsion composition of the present invention, the particle size distribution is wide relative to the peak of the average particle size, or there is another peak in the larger particle size, and it does not contain a large amount of relatively oversized emulsion particles, and there is usually a sharp particle size distribution around the average particle size. Note that an oil-in-water emulsion composition of the present invention with an average particle size of the emulsion particles in a range from 0.1 to 3.5 µm, and an amount of emulsion particles having a particle size of at least 10 times the average particle size in the particle size distribution of the emulsion of less than 5.0% by volume, can be obtained using the production method described below, but the present invention is not limited to this method.

The average particle size of the emulsion particles can be designed as appropriate. However, when using the production method with the vertical batch mixer described below, this can be achieved more advantageously by extending the stirring time after the phase-inversion water and dilution water has been added until the desired average particle size and particle size distribution can be realized.

Because an oil-in-water emulsion composition of the present invention has a fine average particle size and is substantially free of oversized emulsion particles as mentioned above, the adverse effects of emulsion particle agglomeration on storage stability can be minimized, and an emulsion composition is obtained with excellent storage stability, handling and workability, and blending stability. Because the emulsion composition can be obtained using a direct emulsion method, the overall viscosity (=apparent viscosity) of the oil phase composed of component (A) is very high and the emulsion particles are fine and homogeneous. When used, for example, in a cosmetic ingredient, a uniform film consisting of the oil phase can be formed on hair (keratin) and on skin with improved feel. Unlike the emulsion polymerization method, because the oil phase is not a polymer, siloxane oligomers can be removed from the emulsion particles beforehand, and a finer average particle size can be designed for component (A) used in the emulsification process so that the emulsion particles in the oil phase maintain the expected properties of just the oil alone.

Oil-in-Water Emulsion Composition Production Method and Compatible Production Device An oil-in-water emulsion composition of the present invention is preferably obtained by mechanically emulsifying component (A) in water (C) with component (B) using a vertical batch mixer. There are no particular restrictions on the emulsification method, which may be either a phase inversion method or an oil phase dispersion method in a surfactant aqueous solution. Here, the vertical batch mixer is a vertical stirring device that can produce fine, highly uniform emulsion particles by shear force in the dilution process for the aqueous phase during or after phase inversion even when a highly viscous organopolysiloxane or mixture thereof is used as component (A) in the present invention.

The structure of this vertical batch mixer has been proposed in Patent Document 4 and Patent Document 5. In the present invention, use of a vertical concentric multiple-shaft stirrer is preferred which has multiple rotating shafts arranged along the same shaft core. Compared to a non-concentric multiple-shaft vertical batch mixer, a concentric multiple-shaft vertical batch mixture can efficiently and homogeneously emulsify and disperse a highly viscous organopolysiloxane or mixture thereof used as component (A) while effectively preventing adhesion to the container and stirring blades.

A production device particularly suitable to the present invention is a vertical batch mixer with both a ribbon-shaped stirring blade and a non-ribbon-shaped stirring blade. Here, uniform stirring can be performed throughout the entire container by applying strong shear force continuously and uniformly to component (A) to prevent adhesion of component (A) to the container and stirring blades while drawing the component upwards from the bottom of the container. This vertical batch mixer may include supplementary stirring blades, a disperser, and a scraper for removing component (A) from the walls. If structurally possible, a baffle plate may also be provided to increase stirring efficiency.

A production device particularly suitable to the present invention is a concentric multiple shaft vertical batch mixer having multiple rotating shafts arranged along the same shaft core, and comprising a ribbon-shaped stirring blade arranged on at least one rotating shaft and a non-ribbon-shaped stirring blade arranged on a rotating shaft different from this rotating shaft. This can provide an oil-in-water emulsion composition containing the fine emulsion particles described above even when silicone rubber with a viscosity greater than 10,000,000 mPa·s is used. A commercially available version of this device is NANOVisK from Sumitomo Heavy Industries Processing Equipment.

A method for producing an oil-in-water emulsion composition using this vertical batch mixer preferably comprises the following steps.

Step 1: Adding at least some of component (B) to component (A) and mixing

Step 2: Adding at least some of component (C) to the mixture from step 1 and inverting the phase to an oil-in-water emulsion using mechanical force Step 3: Optionally adding more of component (C) to the emulsion composition from step 2 to dilute the aqueous phase while stirring using mechanical force Note that the remaining component (B) and other optional components may be added in step 2 and step 3, and the emulsion particles may be made finer or more homogenous and the presence of oversized particles suppressed by applying shearing force to control the emulsion particles in step 2 and step 3. Also, the emulsion particles may be made finer by adding the phase-inversion water all at once or in stages in step 2 and step 3. Because the shearing force produced by the vertical batch mixer changes depending on the viscosity in the emulsification phase or the dilution phase, the emulsion particles can be made finer or more homogenous by adding the phase-inversion water and dilution water in stages in the same device and at the same stirring speed.

The stirring speed and stirring time in each step can be selected based on the types of component (A) and component (B) used, the desired size of the emulsion particles, and the production scale. Stirring and sampling is preferably performed during step 2 or step 3 of the production process to adjust the emulsion particle size and optimize production conditions.

In the present invention, in an optional step (prior to step 1), an organopolysiloxane or a mixture thereof having an apparent viscosity at 25° C. of less than 1,000,000 mPa·s serving as component (A') or the precursor of component (A) may be added along with a polymerization reaction catalyst to the vertical batch mixer and subjected to a polymerization reaction by stirring at room temperature or under heat to synthesize component (A). In other words, the synthesis process and the emulsification process in the present invention can both be performed in the vertical batch mixer.

Applications for the Oil-in-Water Emulsion Composition

There are no particular restrictions on the applications for an oil-in-water emulsion composition of the present invention, which can be used in a wide range of applications including lubricants, mold release agents, fiber-treating agents, glass fiber-treating agents, cosmetic bases, polishes, and paint additives. By combining an oil-in-water emulsion composition of the present invention with another silicone emulsion or silicone elastomer having a low to medium degree of polymerization, the emulsion composition can be used as a scratch recovery agent with a polishing effect.

An oil-in-water emulsion composition of the present invention can be used advantageously as a cosmetic ingredient, cosmetic, film-forming agent, coating agent, or fiber-treating agent. When used, for example, in a cosmetic ingredient, a uniform film consisting of the oil phase can be formed on hair (keratin) and on skin with improved feel. Because it can be designed to be substantially free of low molecular weight siloxane oligomers from which the impact on the environment is a concern, a wider range of cosmetic formulations can be created with a greater degree of freedom. Because component (A) of the present invention can be a silicone gum widely used as a raw material in cosmetics, cosmetic formulations can be designed that reflect the adhesion and improved feel derived from an oil phase, and can be used in place of hair cosmetics and skin cosmetics with silicone gum emulsions containing oversized emulsion particles which are commonly used as a cosmetic raw material. Improvements in feel, use, and functionality can thus be expected.

Specific cosmetics that can include an oil-in-water emulsion composition of the present invention include skin care products such as skin cleanser products, skin care products, make-up products, antiperspirant products, and UV protection products; hair care products such as hair cleansing products, hair styling products, hair coloring products, hair restoration products, hair rinse products, hair conditioner products, and hair treatment products; and bath products. Drugs containing the present invention may include hair growth agents, hair restorers, analgesics, bactericides, anti-inflammatory agents, freshening agents, and antiaging agents for the skin. There are no restrictions.

Cosmetics that can include an oil-in-water emulsion composition of the present invention can also be applied to those containing conventional silicone rubbers, such as hair cosmetics including oil-in-water emulsions such as shampoos, hair rinses, hair conditioners, and hair treatments. Use of an oil-in-water emulsion composition of the present invention can be expected to improve adhesion of silicone gum to hair and to form a uniform film. Needless to say, any component commonly used in hair cosmetics can also be included.

Many formulations for hair cosmetics containing silicone gums have been disclosed, and the hair cosmetic formulations proposed by the present applicant in JP 2012-046508 A, JP 2012-046507 A, JP 2013-095835 A, JP 2013-095834 A, and JP 2013-095695 A can be designed so that the silicone gums are replaced by compositions containing an organopolysiloxanes with a high degree of polymerization. Formulations and production methods can be easily devised by those skilled in the art if desired.

EXAMPLES

The following is a more detailed description of the present invention with reference to examples and comparative examples, but the present invention is not limited to these examples. In the examples and comparative examples, "parts" refers to "parts by mass". Here, "viscosity" refers to the viscosity (kinematic viscosity) measured at 25° C. using a rotary viscometer. Plasticity was defined above.

In the examples, the rotational speed of the rotating blades is the rotational speed of the non-ribbon blades in FIG. 1. The siloxane oligomer content of the trimethyl-capped dimethylpolysiloxane with a viscosity of 5,000,000 mPa·s or more (plasticity: 120) used in the direct emulsification process is less than 1 mass % in all cases.

The oil-in-water organopolysiloxane emulsion compositions prepared in the examples were evaluated using the following methods and the results are shown in Table 1, along with other types of information.

Average Particle Size of Emulsion Particles

This is the value of the volume average particle size of the emulsion particles of the prepared organopolysiloxane emulsion composition measured using a laser diffraction/scattering type particle size distribution analyzer (Microtrac MT3000II from Microtrac Bell).

Emulsion Particle Size Distribution

The presence and amount of emulsion particles with a particle size at least 10 times greater than the average particle size were confirmed using the same device.

Storage Stability of the Emulsion Composition

The prepared organopolysiloxane emulsion composition was weighed in a 200-cc glass bottle and allowed to stand for two months at 25° C. The state of the emulsion composition was inspected visually. When a uniform phase with no separation was observed, the storage stability was considered good and an "o" was assigned. When separation into two phases was observed, the storage stability was considered poor and an "x" was assigned.

Comparative Example 1

Two types of nonionic surfactant polyoxyethylene lauryl ether (EO moles added: 4 mol): 4.16 parts, 72% by mass aqueous solution of polyoxyethylene lauryl ether (EO moles added: 23 mol): 8.10 parts, and a small amount of water were added to 100.0 parts of trimethyl-capped dimethylpolysiloxane having a viscosity of 5,000,000 mPa·s or more (plasticity: 120). After mixing with a dental mixer, an attempt was made to emulsify the mixture with a colloid mill, which is a pass-through emulsifier, but it could not be processed.

Comparative Example 2

Two types of nonionic surfactant polyoxyethylene lauryl ether (EO moles added: 4 mol): 4.16 parts, 72% by mass aqueous solution of polyoxyethylene lauryl ether (EO moles added: 23 mol): 8.10 parts, and a small amount of water were added to 100.0 parts of trimethyl-capped dimethylpolysiloxane having a viscosity of 5,000,000 mPa·s or more (plasticity: 120). The mixture was placed in a Combimix (from Primix), which is a vertical batch emulsifier, and an attempt was made to mix the mixture, but it could not be processed. The viscosity of the polysiloxane exceeded the available viscosity range of the device.

Example 1

Two types of nonionic surfactant polyoxyethylene lauryl ether (EO moles added: 4 mol): 4.16 parts and 72% by mass aqueous solution of polyoxyethylene lauryl ether (EO moles added: 23 mol): 8.10 parts were added to 100.0 parts of a trimethyl-capped dimethylpolysiloxane with a viscosity of 5,000,000 mPa·s or more (plasticity: 120) and mixed in a 5-liter vertical batch mixer (NANOVisK from Sumitomo Heavy Industries Processing Equipment). After adding a small amount of water to the premix, mixing was performed at a rotating blade speed of 7,200 rpm for 1.5 hours, and then the remaining water was added to obtain an oil-in-water emulsion. The average particle size of the resulting emulsion was 3.8 micrometers, and no emulsion particles with a particle size 10 times greater than the average particle size were detected.

Example 2

Two types of nonionic surfactant polyoxyethylene lauryl ether (EO moles added: 4 mol): 4.16 parts and 72% by mass aqueous solution of polyoxyethylene lauryl ether (EO moles added: 23 mol): 8.10 parts were added to 100.0 parts of a trimethyl-capped dimethylpolysiloxane with a viscosity of 5,000,000 mPa·s or more (plasticity: 120) and mixed in a 5-liter vertical batch mixer (NANOVisK from Sumitomo Heavy Industries Processing Equipment). After adding a small amount of water to the premix, mixing was performed at a rotating blade speed of 7,200 rpm for 2 hours, and then the remaining water was added to obtain an oil-in-water emulsion. The average particle size of the resulting emulsion was 3.4 micrometers, and no emulsion particles with a particle size 10 times greater than the average particle size were detected.

Example 3

Two types of nonionic surfactant polyoxyethylene lauryl ether (EO moles added: 4 mol): 4.16 parts and 72% by mass aqueous solution of polyoxyethylene lauryl ether (EO moles added: 23 mol): 8.10 parts were added to 100.0 parts of a trimethyl-capped dimethylpolysiloxane with a viscosity of 5,000,000 mPa·s or more (plasticity: 120) and mixed in a 5-liter vertical batch mixer (NANOVisK from Sumitomo Heavy Industries Processing Equipment). After adding a small amount of water to the premix, mixing was performed at a rotating blade speed of 7,200 rpm for 3 hours, and then the remaining water was added to obtain an oil-in-water emulsion. The average particle size of the resulting emulsion was 3.2 micrometers, and no emulsion particles with a particle size 10 times greater than the average particle size were detected.

Example 4

Two types of nonionic surfactant polyoxyethylene lauryl ether (EO moles added: 4 mol): 4.16 parts and 72% by mass aqueous solution of polyoxyethylene lauryl ether (EO moles added: 23 mol): 8.10 parts were added to 100.0 parts of a trimethyl-capped dimethylpolysiloxane with a viscosity of 5,000,000 mPa·s or more (plasticity: 152) and mixed in a 5-liter vertical batch mixer (NANOVisK from Sumitomo Heavy Industries Processing Equipment). After adding a small amount of water to the premix, mixing was performed at the same rotating blade speed as [Example 2] (rotating blade speed 7,200 rpm) for 4.5 hours, and then the remaining water was added to obtain an oil-in-water emulsion. The average particle size of the resulting emulsion was 5.1 micrometers, and no emulsion particles with a particle size 10 times greater than the average particle size were detected.

TABLE 1

| | Siloxane Viscosity [mPa · s] (Plasticity [hmm]) | Average Particle Size [μm] | Vol % of Emulsion particles with Avg Particle Size × 10 | Siloxane Mass % in Emulsion | Stability Room Temp. for 2 Mos. |
| --- | --- | --- | --- | --- | --- |
| Ex. 1 | >5,000,000 (120) | 3.8 | Undetected | 65 | ○ |
| Ex. 2 | (120) | 3.4 | | 65 | ○ |
| Ex. 3 | | 3.2 | | 65 | ○ |
| Ex. 4 | >5,000,000 (152) | 5.1 | | 70 | ○ |

As seen in Table 1 (Examples 1-4), by subjecting a trimethyl-capped dimethylpolysiloxane with a viscosity of 5,000,000 mPa·s or more (plasticity: 120 or 152) to direct emulsification, an oil-in-water emulsion composition with an average particle size of 3.2 to 5.1 μm could be obtained, and the resulting emulsion was stable. The particle size distribution was also substantially free of oversized emulsion particles with a particle size 10 times greater than the average particle size. These emulsions could not be realized using the method shown in the comparative examples.

Example 5

Hydroxyl-capped dimethylpolysiloxane (viscosity 1.2 million mPa·s) was synthesized in a 5-liter vertical batch mixer (NANOVisK from Sumitomo Heavy Industries Processing Equipment). Two types of nonionic surfactant polyoxyethylene lauryl ether (EO moles added: 4 mol): 4.16 parts and 72% by mass aqueous solution of polyoxyethylene lauryl ether (EO moles added: 23 mol): 8.10 parts were added and mixed in the same vertical batch mixer. After adding a small amount of water to the premix, mixing was performed at a rotating blade speed of 3,600 rpm for 1.5 hours, and then the remaining water was added to obtain an oil-in-water emulsion. When the average particle size of the resulting emulsion was measured using a Mastersizer 3000 laser diffraction particle size distribution meter (from Malvern), the result was 1.1 micrometers, and no emulsion particles with a particle size 10 times greater than the average particle size were detected.

Formulation Example

The formulations in Table 2 and Table 3 below show a hair care product (shampoo) and skin care product (low viscosity facial toner) using an oil-in-water emulsion composition in the examples of the present application. Cosmetics of the present invention are not limited to these examples. In the tables, "parts" refers to parts by mass.

Formulation Example 1: Shampoo

TABLE 2

|    | Components (Display Name)      | Parts  |
|----|--------------------------------|--------|
| 1  | Water                          | 32.74  |
| 2  | Polyquaternium-10              | 10.00  |
| 3  | Citric Acid                    | 0.06   |
| 4  | EDTA-2Na                       | 0.10   |
| 5  | Glycerin                       | 1.50   |
| 6  | Cocamide MEA                   | 1.00   |
| 7  | Laureth Sulfate Na             | 30.00  |
| 8  | Na Laureth 6-Carboxylate       | 10.00  |
| 9  | Cocamidopropyl Betaine, NaCl   | 10.00  |
| 10 | Polyquaternium-7               | 3.00   |
| 11 | Methyl Isothiazoline           | 0.10   |
| 12 | Cocamide MEA                   | 0.50   |
| 13 | Citric Acid                    | Q.S.   |
| 14 | Oil-in-Water Emulsion of Ex. 1 | 0.50   |

Production Method

1. Mix 1-6 uniformly (using heat if necessary)
2. Add and mix 7, 8 and 9 in order.
3. (After cooling to room temperature if heated), add a mixture of 10, 11 and 12 and then 14 and mix.
4. Add 14 and mix until the pH is 5.5-6.5.

Formulation Example 2: Low Viscosity Facial Toner

TABLE 3

|    | Components (Display Name)                                                                      | Parts  |
|----|------------------------------------------------------------------------------------------------|--------|
|    | Phase A                                                                                        |        |
| 1  | Water                                                                                          | 85.23  |
| 2  | Glycerin                                                                                       | 5      |
| 3  | Ethanol                                                                                        | 5      |
| 4  | (Na Acrylate/Na Acryloyldimethyltaurine) Copolymer, Isohexadecane, Polysorbate 80 Aqueous Solution | 1.07   |
| 5  | Phenoxyethanol                                                                                 | 0.5    |
|    | Phase B                                                                                        |        |
| 6  | Oil-in-Water Emulsion of Ex. 1                                                                 | 2      |
| 7  | Dimethicone (2 mm²/s)                                                                          | 1.2    |

Production Method

1. Mix the components of phase A uniformly.
2. Mix the components of phase B uniformly.
3. While mixing phase A slowly, add phase B.

KEY TO THE DRAWINGS

1, 1': Motor connected to rotational axis
2: Stirring vessel
3: Ribbon stirring blade
4: Non-ribbon stirring blade

The invention claimed is:

1. A method for producing an oil-in-water emulsion composition comprising:
   (A) 100 parts by mass of an organopolysiloxane having a viscosity at 25° C. of at least 1,000,000 mPa·s or having plasticity or a mixture thereof;
   (B1) 0.1 to 30 parts by mass of at least one non-ionic surfactant; and
   (C) 100 to 2,000 parts by mass of water;
   the method comprising mechanically emulsifying component (A) using component (B1) in component (C) using a vertical batch mixer;
   wherein;
   the vertical batch mixer is a concentric multiple shaft vertical batch mixer having multiple rotating shafts arranged along the same shaft core, and comprising a ribbon-shaped stirring blade arranged on at least one rotating shaft and a non-ribbon-shaped stirring blade arranged on a rotating shaft different from this rotating shaft; and
   wherein;
   component (A) is emulsified in water by component (B1) to obtain an emulsion,
   component (B1) is the only surfactant used to produce the oil-in-water emulsion composition and component (B1) comprises polyoxyethylene lauryl ethers;
   the average particle size of the emulsion particles measured using the laser diffraction/scattering method is in a range from 0.1 to 7.5 μm,
   the amount of emulsion particles having a particle size of at least 10 times the average particle size in the particle size distribution of the emulsion is less than 5.0% by volume, and
   the apparent viscosity at 25° C. of the oil phase constituting the emulsion particles is at least 1,000,000 mPa·s or has plasticity.

2. The method for producing an oil-in-water emulsion composition according to claim 1, wherein component (A) is selected from:
   (A1) an organopolysiloxane having a viscosity at 25° C. of at least 1,000,000 mPa·s or having plasticity; or
   (A2) an organopolysiloxane mixture having a viscosity at 25° C. of at least 1,000,000 mPa·s or having plasticity.

3. The method for producing an oil-in-water emulsion composition according to claim 1, wherein component (A) is an organopolysiloxane having a viscosity at 25° C. of at least 2,500,000 mPa·s or having plasticity or a mixture thereof.

4. The method for producing an oil-in-water emulsion composition according to claim 1, wherein the sum of the amount of the siloxane oligomers having a siloxane degree of polymerization of 3 to 6 in the oil phase constituting the emulsion composition is less than 1.0% by mass.

5. A cosmetic ingredient comprising the oil-in-water emulsion composition produced by the method according to claim 1.

6. A cosmetic comprising the oil-in-water emulsion composition produced by the method according to claim 1.

7. A film-forming agent comprising the oil-in-water emulsion composition produced by the method according to claim 1.

8. A coating or coating composition comprising the oil-in-water emulsion composition produced by the method according to claim 1.

9. A fiber-treating agent comprising the oil-in-water emulsion composition produced by the method according to claim 1.

10. The method for producing an oil-in-water emulsion composition according to claim 1, comprising:
   step 1) adding at least some of component (B1) to component (A) and mixing; and
   step 2) adding at least some of component (C) to the mixture from step 1) and inverting the phase to an oil-in-water emulsion using mechanical force; and optionally
   step 3) adding more of component (C) to the emulsion composition from step 2) to dilute the aqueous phase while stirring using mechanical force.

11. The method for producing an oil-in-water emulsion composition according to claim 10, comprising adding the remaining component (B1) and optionally other components in step 2) and step 3).

12. The method for producing an oil-in-water emulsion composition according to claim 1, wherein the method is a direct emulsification method using the vertical batch mixer that does not involve an emulsion polymerization reaction.

13. The method for producing an oil-in-water emulsion composition according to claim 1, wherein the amount of component (B1) used is in a range from 0.5 to 15 parts by mass per 100 parts by mass of component (A).

14. The method for producing an oil-in-water emulsion composition according to claim 1, wherein the oil-in-water emulsion is free of a silicone polyether surfactant.

15. The method for producing an oil-in-water emulsion composition according to claim 1, wherein component (B1) consists of:
   i) a first polyoxyethylene lauryl ether which is prepared from lauryl alcohol and 4 moles of ethylene oxide; and
   ii) a second polyoxyethylene lauryl ether which is prepared from lauryl alcohol and 23 moles of ethylene oxide.

* * * * *